(12) United States Patent
Kojima et al.

(10) Patent No.: US 10,132,746 B2
(45) Date of Patent: Nov. 20, 2018

(54) METHANE NUMBER CALCULATION METHOD AND METHANE NUMBER MEASUREMENT DEVICE

(71) Applicant: Riken Keiki Co. Ltd., Itabashi-ku, Tokyo (JP)

(72) Inventors: Kenichi Kojima, Kasukabe (JP); Tomoo Ishiguro, Kasukabe (JP)

(73) Assignee: Riken Keiki Co. Ltd., Tokyo (JP)

( * ) Notice: Subject to any disclaimer, the term of this patent is extended or adjusted under 35 U.S.C. 154(b) by 0 days.

(21) Appl. No.: 15/531,664

(22) PCT Filed: Mar. 11, 2016

(86) PCT No.: PCT/JP2016/057784
§ 371 (c)(1),
(2) Date: May 30, 2017

(87) PCT Pub. No.: WO2017/013897
PCT Pub. Date: Jan. 26, 2017

(65) Prior Publication Data
US 2017/0370831 A1    Dec. 28, 2017

(30) Foreign Application Priority Data

Jul. 22, 2015 (JP) ................. 2015-144620

(51) Int. Cl.
*G01N 21/35* (2014.01)
*G01N 21/3504* (2014.01)
*G01N 33/22* (2006.01)

(52) U.S. Cl.
CPC ....... *G01N 21/3504* (2013.01); *G01N 33/225* (2013.01); *G01N 2021/3509* (2013.01)

(58) Field of Classification Search
None
See application file for complete search history.

(56) References Cited

U.S. PATENT DOCUMENTS 5,822,058 A * 10/1998 Adler-Golden ...... G01N 21/359
356/303
6,279,380 B1 * 8/2001 Van Wesenbeeck .........
G01N 33/225
73/23.31
(Continued)

FOREIGN PATENT DOCUMENTS

EP          1193488 A1    4/2002
JP       54-130990 A    10/1979
(Continued)

OTHER PUBLICATIONS

T. Matsushita, et al; Genba Needs o Tsuikyu shita Field Keiso Tool—Kaihatsu no Nerai to Un'yo . . . ; vol. 53; No. 5; May 2010; 5 pages.
(Continued)

*Primary Examiner* — Edwin Gunberg
(74) *Attorney, Agent, or Firm* — Lucas & Mercanti, LLP

(57) ABSTRACT

The present invention has as its object the provision of a methane number calculation method that allows for readily acquiring a methane number of a natural gas, which is a sample gas to be measured, with acceptable reliability irrespective of toe gas composition, and as another object the provision of a methane number measurement device that is capable of monitoring the fuel property of a natural gas to be used as a fuel gas.

The present invention includes: acquiring in advance a particular relational expression between the methane number and the basic calorific value of a plurality of types of reference gases, each formed of a natural gas and each having a different methane number value; measuring the basic calorific value of a natural gas, which is a sample gas, as well as the concentration of the nitrogen gas and the concentration of the carbon dioxide gas, both gases being contained in the sample gas; and calculating the methane
(Continued)

number of the sample gas from the value of the basic calorific value of the sample gas, the value of the concentration of the nitrogen gas and the value of the concentration of the carbon dioxide gas, and the particular relational expression.

8 Claims, 1 Drawing Sheet

(56) References Cited

U.S. PATENT DOCUMENTS

| | | | |
|---|---|---|---|
| 6,286,360 B1* | 9/2001 | Drzewiecki | A61B 5/083 |
| | | | 702/24 |
| 2002/0124630 A1 | 9/2002 | Jaeschke et al. | |
| 2004/0195531 A1 | 10/2004 | Rahmouni et al. | |

FOREIGN PATENT DOCUMENTS

| | | |
|---|---|---|
| JP | 10185887 A | 7/1998 |
| JP | 2009042216 A | 2/2009 |
| JP | 2011502250 A | 1/2011 |
| WO | 2010013303 A1 | 2/2010 |

OTHER PUBLICATIONS

International Search Report dated May 31, 2016 for PCT/JP2016/057784.
Extended European Search Report dated Jul. 2, 2018 from corresponding European Application No. EP 16827462.9.
Schley P. et al, Bestimmung der Methanzahl aus GasbeschaffenheitskenngroBen, GWF GAS/ERDGAS, vol. 141, No. 1; 2000, pp. 28-33, XP9506258, paragraph [4.2.].
ISO/TR 22302, 2014 Natural gas-Calculation of methane number, XP9506254, paragraphs [3.1.]-[4.1].

* cited by examiner

METHANE NUMBER CALCULATION METHOD AND METHANE NUMBER MEASUREMENT DEVICE

CROSS REFERENCE TO RELATED APPLICATION

This Application is a 371 of PCT/JP2016/057784 filed on Mar. 11, 2016 which, in turn, claimed the priority of Japanese Patent Application No. 2015-144620 filed Jul. 22, 2015, all applications are incorporated herein by reference.

TECHNICAL FIELD

The present invention relates to a methane number calculation method and a methane number measurement device.

BACKGROUND ART

Recently, gas engines that operate on a natural gas serving as a fuel have been being developed and introduced in order to cut the amount of emission of nitrogen oxide (NOx) or to reduce the amount of emission of $CO_2$.

As examples of the problems to be addressed in order to bring the gas engine operating on a natural gas into practical use, may be mentioned the following: that the compositions of natural gases may be different depending on where the gases are produced; and that the composition of a fuel gas may vary by the amount of consumption of the fuel gas being varied at the start of the gas engine or when variation in load occurs. A change in the composition of a fuel gas would lead to a change in the properties of the fuel gas such as the calorific value or the methane number, thereby causing an abnormal combustion such as engine knocking or misfire. Here, the methane number is an indicator which indicates the resistance value to knocking corresponding to the octane number of a gasoline engine and which is evaluated as 100 for pure methane and 0 for hydrogen.

In order to avoid such an abnormal combustion, it is considered as effective means to acquire the fuel properties of the fuel gas such as the calorific value or the methane number in real time so as to provide combustion control to the gas engine on the basis of the data.

For example, the present applicant has suggested a method of measuring the calorific value of a fuel gas such as a natural gas, the method including: measuring, for example, a physical property value having a particular correlation with the calorific value; and determining the value of calorific value on the basis of the measurement value (converted calorific value) (refer to Patent Literature 1, for example).

On the other hand, mainly employed as a method of calculating the methane number of a fuel gas are the following four types:

(a) A scheme suggested by AVL (hereafter, also referred to as "the AVL Standard");

(b) A scheme of calculating by a particular arithmetic expression specified by California Air Resources Board (hereafter, also referred to as "the CARE Standard");

(c) A scheme of calculating by a method in conformity to ISO/TR 22302 3.1.1 (hereafter, also referred to as "the GRI (Lc) Standard"); and (d) A scheme of calculating by a method in conformity to ISO/TR 22302 3.1.2 (hereafter also referred to as "the GRI (H/C) Standard"). Here, the methane numbers of the same fuel gas may exhibit different values depending on the calculation methods, and for example, a methane number based on a different standard by area is demanded. However, in any of the methods, it is necessary to measure the gas composition in calculating the methane number when a variation occurs in gas composition, since the methods are to calculate the methane number on the basis of the gas composition, as described above.

CITATION LIST

Patent Literature

Patent Literature 1: Japanese Patent Application Laid-Open No. 2009-42216

SUMMARY OF INVENTION

Technical Problem

Well, a natural gas typically contains not only a combustible gas component such as a paraffinic hydrocarbon gas but also an inert gas component such as a nitrogen gas or carbon dioxide gas. Since no regularity is found in the degree of influence on the amount of heat generated by these inert gas components, no particular correlation can be established between the amount of heat generation (true calorific value) and the value of the methane number of the natural gas. Furthermore, since the concentration ratio between the nitrogen gas and the carbon dioxide gas contained in a natural gas cannot be quantified, there will unavoidably occur a calculation error that is caused by these miscellaneous gas components being contained.

However, as a result of studies intensively conducted by the inventors, it was found that a particular correlation is established between the nitrogen gas concentration contained in a natural gas and the amount of variation (error) in methane number caused by the nitrogen gas concentration, and that a particular correlation is established between the carbon dioxide gas concentration contained in a natural gas and the amount of variation (error) in methane number caused by the carbon dioxide gas concentration. It was thus found that by making a correction depending on each of the nitrogen gas concentration and the carbon dioxide gas concentration, a particular correlation is established between the value of the basic calorific value of a natural gas and the value of the methane number calculated, by the AVL Standard mentioned above, for example, so that by measuring the basic calorific value of a natural gas, which is a sample gas, it is possible to acquire an approximate solution to the methane number corresponding to the AVL Standard. Here, "the basic calorific value" refers to the combustion calorific value of the combustible gas component acquired by removing the inert gas components from the natural gas.

The present invention has been made in view of the aforementioned circumstances, and has as its object the provision of a methane number calculation method that allows for readily acquiring a methane number of a natural gas, which is a sample gas to be measured, with acceptable reliability irrespective of the gas composition.

The present invention has as another object the provision of a methane number measurement device which is capable of readily acquiring a methane number of a natural gas, which is a sample gas, with acceptable reliability irrespective of the gas composition, and which is capable of monitoring the fuel property of the natural gas to be used as a fuel gas.

Solution to Problem

A methane number calculation method according to the present invention includes: acquiring in advance a particular relational expression between a methane number and a basic calorific value of a plurality of types of reference gases, each formed of a natural gas and each having a different value of the methane number;

measuring a basic calorific value of a natural gas, which is a sample gas to be measured, and measuring a concentration of a nitrogen gas and a concentration of a carbon dioxide gas, the nitrogen gas and the carbon dioxide gas being contained in the sample gas; and calculating a methane number of the sample gas from a value of the basic calorific value of the sample gas, a value of the concentration of the nitrogen gas and a value of the concentration of the carbon dioxide gas, and the particular relational expression.

The methane number calculation method according to the present invention adopts, as the particular relational expression, one that is expressed by a formula (1) described below:

[Mathematical Expression 1]

$$MN = f_{(Q')} + A \qquad \text{Formula (1)}$$

provided that, in the formula (1), MN is the methane number, $f_{(Q')}$ is any one of the functions expressed by a formula (a) to a formula (d) below to be selected depending on the value of the basic calorific value Q'[MJ/m³] of the sample gas, and "A" is a value to be selected within a range of −2.0 to 2.0.

[Mathematical Expression 2]

$$f_{(Q')} = -0.529862 Q'^3 + 67.1872 Q'^2 - 2845.15 Q' + 40316.8 + 0.32 X_{N_2} + 1.00 X_{CO_2} \; (Q' \leq 42.0) \qquad \text{Formula (a)}$$

$$f_{(Q')} = -0.006745 Q'^3 + 1.11764 Q'^2 - 62.9206 Q' + 1252.43 + 0.32 X_{N_2} + 1.00 X_{CO_2} \; (42.0 < Q' \leq 55.0) \qquad \text{Formula (b)}$$

$$f_{(Q')} = -0.001547 Q'^3 + 0.293255 Q'^2 - 19.1911 Q' + 475.981 + 0.32 X_{N_2} + 1.00 X_{CO_2} \; (55.0 < Q' \leq 63.0) \qquad \text{Formula (c)}$$

$$f_{(Q')} = 0.000278 Q'^3 + 0.072315 Q'^2 - 6.44881 Q' + 232.610 + 0.32 X_{N_2} + 1.00 X_{CO_2} \; (63.0 < Q') \qquad \text{Formula (d)}$$

provided that, in the formula (a) to the formula (d), $X_{N2}$ is the concentration of the nitrogen gas contained in the sample gas and expressed in volume percentage [vol %] and $X_{CO2}$ is the concentration of the carbon dioxide gas contained in the sample gas expressed in volume percentage [vol %].

Furthermore, in the methane number calculation method according to the present invention, the basic calorific value of the sample gas is preferably acquired on the basis of a refractive index converted calorific value acquired from a refractive index of the sample gas and a sonic speed converted calorific value acquired from a sonic speed of the sample gas.

Still furthermore, in the methane number calculation method according to the present invention, the concentration of the carbon dioxide gas contained in the sample gas is preferably measured by an infrared absorption method.

A methane number measurement device according to the present invention includes:

a calorific value measurement mechanism for measuring a basic calorific value of a natural gas, which is a sample gas to be measured;

a carbon dioxide concentration measurement mechanism for measuring a concentration of a carbon dioxide gas contained in the sample gas;

a nitrogen concentration calculation mechanism for calculating a concentration of a nitrogen gas contained in the sample gas; and a methane number calculation mechanism for calculating a methane number of the sample gas from a particular relational expression acquired in advance, between a methane number and a basic calorific value of a plurality of types of reference gases, each formed of a natural gas and each having a different value of the methane number, and from a value of the basic calorific value of the sample gas which is measured by the calorific value measurement mechanism, a value of the concentration of the carbon dioxide gas measured by the carbon dioxide concentration measurement mechanism, and a value of the concentration of the nitrogen gas calculated by the nitrogen concentration calculation mechanism.

In the methane number measurement device according to the present invention, the particular relational expression is preferably expressed by the formula (1) described above.

Furthermore, in the methane number measurement device according to the present invention, the calorific value measurement mechanism is preferably configured to include: refractive index converted calorific value measurement unit configured to determine a refractive index converted calorific value from a refractive index value of the sample gas; sonic speed converted calorific value measurement unit configured to determine a sonic speed converted calorific value from a sonic speed value of the sample gas; and calorific value calculation unit configured to calculate the basic calorific value of the sample gas on the basis of the refractive index converted calorific value and the sonic speed converted calorific value.

Still furthermore, in the methane number measurement device according to the present invention, the carbon dioxide concentration measurement mechanism preferably includes an infrared sensor.

Advantageous Effects of Invention

According to the methane number calculation method of the present invention, by employing a particular relational expression acquired in advance between the basic calorific value and the methane number, it is possible to determine the methane number of the sample gas on the basis of the basic calorific value value of the sample gas. The particular relational expression was experimentally supported by taking into account the influence on the basic calorific value due to a miscellaneous gas component such as a nitrogen gas and a carbon dioxide gas contained in a natural gas so as to quantitatively clarify the correlation between the basic calorific value and the methane number of a plurality of types of reference gases, each having a mutually different methane number value and formed of a natural gas. This, the resulting methane number is to be provided with acceptable reliability.

According to the methane number measurement device of the present invention in which the methane number calculation method mentioned above is executed, the basic calorific value of a sample gas is continuously measured by the calorific value measurement mechanism, thereby enabling continuous acquirement of the methane number of the sample gas in keeping with the actual situation. This allows for monitoring the actual fuel property of the natural gas serving as a fuel gas. Thus, when a variation in gas composition has occurred, it is possible to quickly detect a variation in methane number caused by the variation in gas composition.

DESCRIPTION OF EMBODIMENTS

An embodiment of the present invention will now be described below in more detail.

Figure 1:
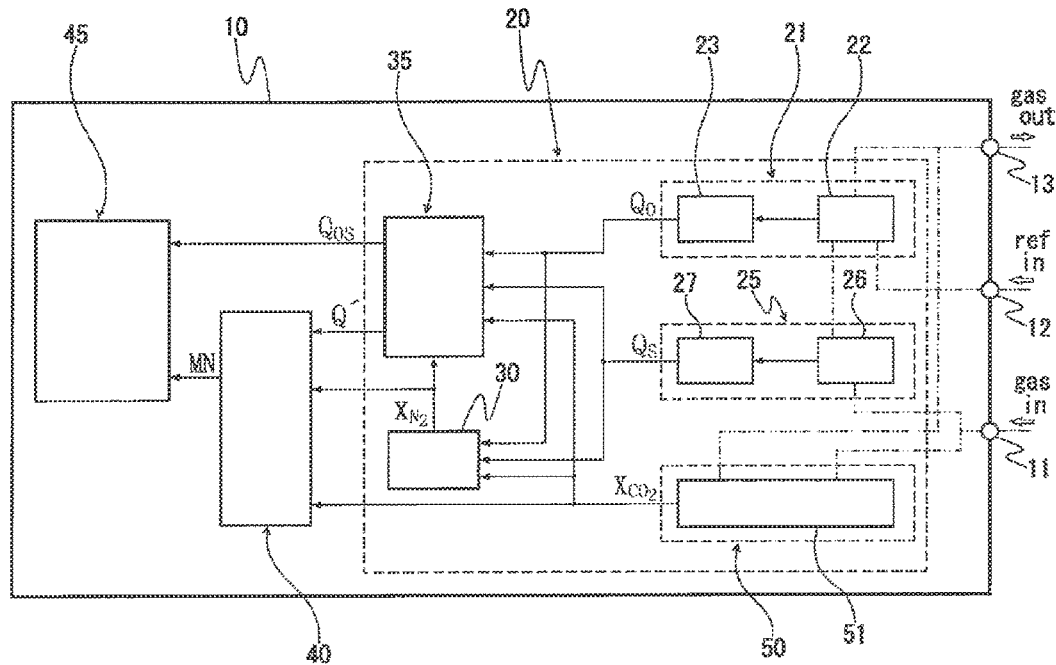
[FIG. 1] is a block diagram schematically illustrating a configuration of an example of a methane number measurement device according to the present invention.

FIG. 1 is a block diagram schematically illustrating the configuration of an example methane number measurement device of the present invention.

This methane number measurement device employs a natural gas as a sample gas to be measured and is configured to include a calorific value measurement mechanism 20 for measuring a calorific value of the sample gas, a methane number calculation mechanism 40 for calculating a methane number of the sample gas, and a display mechanism 45 for displaying information such as the calorific value and the methane number of the sample gas. These mechanisms are disposed, for example, in an outer container 10.

In an example, the calorific value measurement mechanism 20 includes a refractive index converted calorific value measurement mechanism 21 for acquiring a refractive index converted calorific value $Q_O$ determined from a refractive index value of a natural gas, which is a sample gas; a sonic speed converted calorific value measurement mechanism 25 for acquiring a sonic speed converted calorific value $Q_S$ determined from a sonic speed value of the sample gas; a carbon dioxide concentration measurement mechanism 50 for measuring the concentration $X_{CO2}$ of a carbon dioxide gas contained in the sample gas; a nitrogen concentration calculation mechanism 30 for calculating the concentration $X_{N2}$ of a nitrogen gas contained in the sample gas; and a calorific value calculation mechanism 35 for calculating a value of the calorific value $Q_{OS}$ and a value of the basic calorific value Q' of the sample gas.

The refractive index converted calorific value measurement mechanism 21 includes refractive index measurement means 22 for measuring the refractive index of the sample gas and refractive index-to-calorific value conversion means 23 having the function of determining the refractive index converted calorific value $Q_O$ on the basis of the refractive index value measured by the refractive index measurement means 22.

The refractive index-to-calorific value conversion means 23 calculates the refractive index converted calorific value $Q_O$ of the sample gas. This is done by employing the correlation between the refractive index and the calorific value of a particular gas formed of only a combustible gas component (paraffinic hydrocarbon gas) that contains no inert gas component (for example, $N_2$ or $CO_2$) in the natural gas, which is a sample gas that has been acquired in advance by drawing a graph, for example, and then, assuming that the value of the refractive index acquired for the sample gas is the refractive index of the particular gas, contrasting the refractive index with the calorific value in the correlation.

The sonic speed converted calorific value measurement mechanism 25 includes: sonic speed measurement means 26 for measuring the propagation speed of sound waves in the sample gas (the sonic speed of the sample gas); and sonic speed-to-calorific value conversion means 27 having the function for determining the value of the sonic speed converted calorific value $Q_S$ on the basis of the value of the sonic speed measured by the sonic speed measurement means 26.

The sonic speed-to-calorific value conversion means 27 calculates the sonic speed converted calorific value $Q_S$ of the sample gas. This is done by employing the correlation between the sonic speed and the calorific value of a particular gas formed of only a combustible gas component (paraffinic hydrocarbon gas) that contains no inert gas component (for example, $N_2$ or $CO_2$) in the natural gas, which is a sample gas that has been acquired in advance by drawing a graph, for example, and then, assuming that the value of the sonic speed acquired for the sample gas is the sonic speed of the particular gas, contrasting the sonic speed with the calorific value in the correlation.

The carbon dioxide concentration measurement mechanism 50 includes carbon dioxide concentration measurement means 51 for measuring the concentration $X_{CO2}$ of a carbon dioxide gas contained in a natural gas, which is a sample gas.

For example, without limitation, the carbon dioxide concentration measurement means 51 is preferably configured to include an infrared sensor which detects the concentration $X_{CO2}$ of a carbon dioxide gas depending on the level of attenuation of the quantity of infrared light that is caused by the infrared light being absorbed by the carbon dioxide gas or the gas to be sensed. Employing, as the carbon dioxide concentration measurement means 51, one that follows the so-called non-dispersive infrared absorption method allows for reducing as much as possible the influence of other miscellaneous gases contained in the sample gas. It is thus possible to detect the concentration $X_{CO2}$ of the carbon dioxide gas with high precision.

On the basis of the value of the refractive index converted calorific value $Q_O$ acquired by the refractive index converted calorific value measurement mechanism 21, the value of the sonic speed converted calorific value $Q_S$ acquired by the sonic speed converted calorific value measurement mechanism 25, and the value of the concentration $X_{CO2}$ of the carbon dioxide gas acquired by the carbon dioxide concentration measurement mechanism 50, the nitrogen concentration calculation mechanism calculates the concentration $X_{N2}$ of a nitrogen gas contained in the natural gas, which is a sample gas, by the formula (2) described below, under the condition of using a value of a correction factor α selected within a range of 1.1 to 4.2, preferably within a range of 2.00 to 2.60. For example, the refractive index converted calorific value $Q_O$ and the sonic speed converted calorific value $Q_S$ of each of miscellaneous gas components (for example, a nitrogen gas and a carbon dioxide gas) contained in the sample gas are actually measured, and then, the value of the correction factor α is set on the basis of the error ratio of the resulting refractive index converted calorific value $Q_O$ and the resulting sonic speed converted calorific value $Q_S$ to the calorific value acquired, for example, by analysis using gas chromatography. Here, the value of the correction factor α takes on a different value depending on the type of a miscellaneous gas component contained in the sample gas. However, the value is selected from within the aforementioned numerical value range, thereby enabling proper correction of an error that may occur in each of the measurements of the refractive index converted calorific value $Q_O$ and the sonic speed converted calorific value $Q_S$.

[Mathematical Expression 3]

$$X_{N_2} = \frac{100}{k_{N_2}} \left( \frac{Q_O - Q_S}{1-\alpha} - \frac{k_{CO_2} X_{CO_2}}{100} \right) \quad \text{Formula (2)}$$

In the formula (2) described above, $X_{N2}$ is the concentration of the nitrogen gas expressed in volume percentage [vol %]. The "$k_{N2}$" which is an error coefficient of a nitrogen gas, represents the magnitude of the influence of an error that $N_2$ as a miscellaneous gas component may exert on the refractive index measurement means 22. The "$k_{CO2}$" which is an error coefficient for a carbon dioxide gas, represents the magnitude of the influence of an error that $CO_2$ as a miscellaneous gas component may exert on the refractive index measurement means 22. The unit of the value of the refractive index converted calorific value $Q_O$ and the value of the sonic speed converted calorific value $Q_S$ to be served for calculation is [MJ/Nm³]. The unit of the value of the concentration $X_{CO2}$ of a carbon dioxide gas is [vol %].

The error coefficient $k_{N2}$ of a nitrogen gas is a value that is selected, for example, within the range of 20.00 to 30.00. Furthermore, the error coefficient $k_{CO2}$ of a carbon dioxide gas is a value that is selected, for example, within the range of 35.00 to 45.00. The error coefficient $k_{N2}$ of a nitrogen gas and the error coefficient $k_{CO2}$ of a carbon dioxide gas are selected within the aforementioned numerical value range, thereby enabling proper correction of an error that may occur in the measurement of the refractive index converted calorific value $Q_O$.

More specifically, for example, the refractive index converted calorific value $Q_O$ of a nitrogen gas (100 vol %) can be actually measured by the refractive index converted calorific value measurement mechanism 21, and on the basis of the resulting value, the value of the error coefficient $k_{N2}$ of a nitrogen gas can be set. On the other hand, likewise, for example, the refractive index converted calorific value $Q_O$ of a carbon dioxide gas (100 vol %) can be actually measured by the refractive index converted calorific value measurement mechanism 21, and on the basis of the resulting value, the value of the error coefficient $k_{CO2}$ of a carbon dioxide gas can be set.

The calorific value calculation mechanism 35 calculates the value of the calorific value $Q_{OS}$ of a natural gas, which is a sample gas, on the basis of the value of the refractive index converted calorific value $Q_O$ acquired by the refractive index converted calorific value measurement mechanism 21 and the value of the sonic speed converted calorific value $Q_S$ acquired by the sonic speed converted calorific value measurement mechanism 25. More specifically, for the refractive index converted calorific value $Q_O$ having a magnitude not more than the sonic speed converted calorific value $Q_S$ ($Q_O \leq Q_S$), the value of the calorific value $Q_{OS}$ is calculated by a formula (3) below, under the condition of using a value of the correction factor α selected within the range of 1.1 to 4.2, preferably within the range of 2.00 to 2.60. On the other hand, for the value of the refractive index converted calorific value $Q_O$ being greater than the value of the sonic speed converted calorific value $Q_S$ ($Q_O > Q_S$), the value of the refractive index converted calorific value $Q_O$ is employed as the value of the calorific value $Q_{OS}$.

[Mathematical Expression 4]

$$Q_{OS} = Q_O - \frac{Q_O - Q_S}{1-\alpha}(Q_O \leq Q_S) \quad \text{Formula (3)}$$

Furthermore, on the basis of the value of the calorific value $Q_{OS}$ acquired in this manner, the value of the concentration $X_{CO2}$ of the carbon dioxide gas acquired by the carbon dioxide concentration measurement mechanism 50, and the value of the concentration $X_{N2}$ of the nitrogen gas acquired by the nitrogen concentration calculation mechanism 30, the calorific value calculation mechanism 35 calculates, by a formula (4) below, the value of the basic calorific value Q'[MJ/Nm³].

[Mathematical Expression 5]

$$Q' = \frac{Q_{OS}}{1-(0.01X_{N_2}+0.01X_{CO_2})} \quad \text{Formula (4)}$$

The methane number calculation mechanism 40 calculates the methane number MN of a natural gas, which is a sample gas, more specifically, an approximate solution to the value of the methane number that is acquired by the method based on the aforementioned AVL Standard (Standard (a)).

On the basis of the value of the basic calorific value Q' of the sample gas, which is measured by the calorific value measurement mechanism 20, and from a particular relational expression acquired in advance between the value of the basic calorific value Q' and the value of the methane number (AVL value) by a method based on the AVL Standard for a plurality of types of reference gases, the methane number calculation mechanism 40 calculates the methane number MN as an approximate solution to the AVL value of the natural gas, which is the sample gas. The plurality of types of reference gases are each formed of a natural gas having a different value of the methane number MN based on the AVL Standard.

In the coordinate system with the horizontal axis representing the basic calorific value Q'[MJ/Nm³] and the vertical axis representing the methane number (AVL value) MN, the particular relational expression can be acquired by acquiring a measured value indicative of the relation between the value of the basic calorific value Q' and the value of the methane number MN for each of the plurality of types of reference gases, and then, for example, by performing curve approximation with a polynomial expression on the resulting measured value. More specifically, the particular relational expression is preferably expressed by the formula (1) described above.

In the formula (1) described above, MN is the methane number, more specifically, an approximate solution to the AVL value, and $f_{(Q')}$ is one of the functions expressed by the formula (a) to the formula (d) described above that is selected depending on the value of the basic calorific value Q' of the sample gas. In the formula (a) to the formula (d) described above, $X_{N2}$ is the concentration of a nitrogen gas contained in the sample gas and is expressed in volume percentage [vol %], and $X_{CO2}$ is the concentration of a carbon dioxide gas contained in the sample gas and is expressed in volume percentage [vol %].

In the formula (1) described above, "A" is a value that is selected from within the range of −2.0 to 2.0. The range of numerical values that are set to "A" indicates a practical tolerance, in which a correction is made in keeping with the fuel property of an actual LNG vaporized gas, of a reference methane number calculation curve itself expressed by the formula (1) with A=0. As shown in the results of an experimental example to be discussed later, if a value of "A" falls within the aforementioned numerical value range, the error ratio of the calculated approximate solution to the AVL value is within 5.0%, providing high reliability. For example, as a specific method of setting the value of "A" in the formula (1) described above, it is possible to measure the methane number of a reference gas with known compositions and then set the difference between the methane number and a theoretical value (the AVL value) as "A" (make an offset adjustment).

Figure 2:
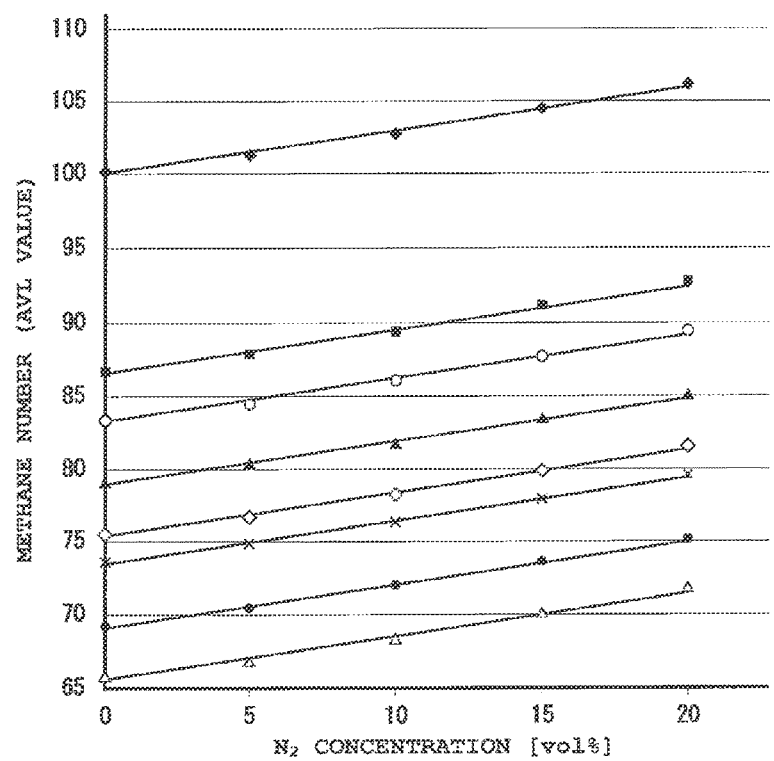
[FIG. 2] is a graph indicative of the relation between a nitrogen gas concentration and a methane number (the AVL Standard).

The term "0.32 $X_{N2}$" in the formula (a) to the formula (d) described above is indicative of the amount of correction of the methane number based on the measured nitrogen gas concentration $X_{N2}$. For example, as shown in FIG. 2, in the coordinate system with the horizontal axis representing the concentration expressed in the volume percentage of a nitrogen gas contained in the sample gas [vol %] and the vertical axis represent no the methane number (the AVL value), the amount of correction of the methane number was set on the basis of an approximate straight line acquired by acquiring a measured value indicative of the relation between the concentration value $X_{N2}$ of a nitrogen gas and the AVL value for each of the plurality of types of reference gases having mutually different methane number values, and performing, for example, linear approximation of the resulting measured value. As can be seen clearly from FIG. 2, it is understood that the approximate curves for the respective reference gases have a gradient of mutually the same magnitude, and the magnitude of the gradient is set as the correction factor "0.32" for the nitrogen gas. Note that FIG. 2 is a graph acquired by employing a mixture gas of $CH_4$ with any one or more of $C_2H_6$, $C_3H_8$ and $N_2$, having appropriately changed the concentration of each gas component.

The term "1.00$X_{CO2}$" in the formula (a) to the formula (d) described above is indicative of the amount of correction of the methane number based on the measured carbon dioxide gas concentration $X_{CO2}$. The amount of correction of the methane number for a carbon dioxide gas is set by the same method as that for the amount of correction of the methane number for the nitrogen gas. For the carbon dioxide gas, the approximate curves of the respective reference gases have the gradient of mutually the same magnitude, and the magnitude of the gradient is set as a correction factor "1.00" for the carbon dioxide gas.

In the foregoing, a natural gas, which is a sample gas, may contain, for example, an oxygen gas as a miscellaneous gas component. However, since a natural gas contains only a trace amount of oxygen gas, the influence of the oxygen gas on the methane number can be substantially ignored.

In the foregoing, FIG. 1 shows an inlet port 11 for a sample gas for supplying the sample gas to each of the refractive index measurement means 22, the sonic speed measurement means 26, and the carbon dioxide concentration measurement means 51. Also shown are an inlet port 12 for a reference gas for introducing a reference gas that is required, from a detection principle viewpoint, in the refractive index measurement means 22, and numeral 13 denotes a gas outlet. On the other hand, the chain double-dashed line of FIG. 1 is indicative of a gas pipe.

For example, the methane number measurement device described above is piped to a gas pipeline via an appropriate gas sampling device and allows part of a natural gas flowing through the gas pipeline to be sequentially supplied, as a sample gas, from the inlet port 11 for the sample gas to each of the sonic speed measurement means 26 of the sonic speed converted calorific value measurement mechanism 25 and the refractive index measurement means 22 of the refractive index converted calorific value measurement mechanism 21. Furthermore, for example, a reference gas such as air is supplied from the inlet port 12 for the reference gas to the refractive index measurement means 22 of the refractive index converted calorific value measurement mechanism 21. Thus, the refractive index converted calorific value measurement mechanism 21 allows the refractive index measurement means 22 to measure the refractive index of the natural gas, and on the basis of the result, the refractive index converted calorific value $Q_O$ is determined by the refractive index-to-calorific value conversion means 23. Furthermore, the sonic speed converted calorific value measurement mechanism 25 allows the sonic speed measurement means 26 to measure the sonic speed of the natural gas, and on the basis of the result, the value of the sonic speed converted calorific value $Q_S$ is determined by the sonic speed-to-calorific value conversion means 27.

On the other hand, all the other of the natural gas introduced from the inlet port 11 for the sample gas is supplied to the carbon dioxide concentration measurement means 51 of the carbon dioxide concentration measurement mechanism 50. Thus, the carbon dioxide concentration measurement mechanism 50 allows the carbon dioxide concentration measurement means 51 to measure the concentration $X_{CO2}$ [vol % (volume percentage)] of a carbon dioxide gas contained in the natural gas.

On the basis of the value of the refractive index converted calorific value $Q_O$ and the value of the sonic speed converted calorific value $Q_S$, which are acquired as described above, the concentration $X_{N2}$ of the nitrogen gas and the calorific value $Q_{OS}$ are calculated by the formula (2) and the formula (3) described above using the value selected within a particular range as the correction factor α. Then, on the basis of the value of the calorific value $Q_{OS}$, the value of the concentration $X_{CO2}$ of the carbon dioxide gas, and the value of the nitrogen gas concentration $X_{N2}$, the basic calorific value Q' of the sample gas is calculated by the formula (4) described above.

Then, on the basis of the aforementioned particular relational expression (the function of any of the formula (a) to the formula (d)) selected depending on the value of the basic calorific value Q' acquired by the calorific value measurement mechanism 20, the methane number calculation mechanism 40 calculates the methane number MN as an approximate solution to the AVL value, and the result is displayed on the display mechanism 45.

Note that the sample gas and the reference gas are discharged out of the device through the gas outlet 13.

Then, according to the aforementioned methane number calculation method, the particular relational expression acquired in advance between the basic calorific value Q' and the methane number MN can be employed to determine the methane number MN of the sample gas on the basis of the basic calorific value Q' of the sample gas. The particular relational expression was experimentally supported by taking into account the influence due to the inclusion of the nitrogen gas and the carbon dioxide gas so as to quantitatively clarify the correlation between the value of the basic calorific value and the AVL value for a plurality of types of reference gases formed of natural gases each having a mutually different value of the methane number based on the AVL Standard (the AVL value). Thus, the resulting methane number MN has an acceptable reliability.

Thus, according to the aforementioned methane number measurement device configured to execute such a methane number calculation method, the calorific value measurement mechanism 20 continuously measures the basic calorific value Q' of the sample gas, thereby allowing the methane number MN to be continuously acquired as an approximate solution to the AVL value of the sample gas in keeping with the actual situation. It is thus possible to monitor the actual fuel property of the natural gas serving as a fuel gas. Thus, when a variation in gas composition occurs, it is possible to quickly detect a variation in the methane number MN caused by the variation in the gas composition.

Furthermore, since the aforementioned methane number measurement device is configured in a manner such that the calorific value measurement mechanism 20 and the methane number calculation mechanism 40 are provided in the outer container 10, the measurement system can be constructed and operated in a simplified fashion. Furthermore, considerable time will never be required to make a measurement.

Furthermore, since there occurs no time lag between the calculation of the basic calorific value Q' and the calculation of the methane number MN, the methane number MN can be measured in real time.

Still furthermore, the calorific value measurement mechanism 20 is configured to calculate the calorific value of the sample gas on the basis of two converted heat quantities, i.e., the refractive index converted calorific value $Q_O$ and the sonic speed converted calorific value $Q_S$. Thus, since the resulting calorific value $Q_{OS}$ takes on a value that has a small difference from the true value of the calorific value of the sample gas irrespective of the gas composition of the sample gas, the calculated methane number MN has a more highly reliable value.

In the foregoing, the embodiment of the present invention has been described. However, the present invention is not limited to the aforementioned embodiment and may be subjected to various modifications.

In the present invention, the calorific value measurement mechanism is not limited to that of the aforementioned configuration. It is also acceptable to use a device that is configured to determine the value of the calorific value on the basis of the value of the thermal conductivity converted calorific value and the value of the refractive index converted calorific value. It may also be acceptable to employ a device that is configured to measure one of physical property values having a particular correlation with the calorific value, for example, one value selected from the refractive index, the thermal conductivity, and the sonic speed and to determine the calorific value on the basis of the measured value. It s also possible to acquire the methane number within a predetermined tolerance for the value of the methane number based or each reference even by using the value of the basic calorific value calculated on the basis of the calorific value of the sample gas which has been acquired in this manner.

Now, an experimental example of the present invention will be described below.

Experimental Example 1

Nineteen types of sample gases (A to S) having the gas compositions shown in Table 1 described below were prepared, and then the methane number of each of the sample gases A to S was measured using the methane number measurement device configured as shown in FIG. 1. In calculating the methane numbers, using a particular relational expression of the formula (1) as above in which A=0, the formulas were selected as follows: the formula (a) described above when the value of the basic calorific value Q' of the sample gas was not more than 42.0 [MJ/Nm$^3$]; the formula (b) described above when the value of the basic calorific value Q' was more than 42.0 [MJ/Nm$^3$] and not more than 55.0 [MJ/Nm$^3$]; the formula (c) described above when the value of the basic calorific value Q' was more than 55.0 [MJ/Nm$^3$] and not more than 63.0 [MJ/Nm$^3$]; and the formula (d) described above when the value of the basic calorific value Q' was more than 63.0 [MJ/Nm$^3$]. Furthermore, in the formula (2) and the formula (3) described above, the correction factor α was 2.24, and in the formula (2), the error coefficient $k_{N2}$ was 26.06 for the nitrogen gas and the error coefficient $k_{CO2}$ was 40.53 for the carbon dioxide gas.

Then, for each of the sample gases A to S, by the method based on the AVL Standard (the methane number calculation software provided by AVL), when the methane number calculated on the basis of the gas composition is employed as a true value, an error of the value of the methane number calculated on the basis of the basic calorific value (the calorific value converted value) to the true value was calculated. The results are shown in Table 1 below. The error was obtained by subtracting the true value from the calorific value converted value.

TABLE 1

| Sample gas | Composition [vol %] | | | | | Methane number (AVL Standard) | |
|---|---|---|---|---|---|---|---|
| | $N_2$ | $CO_2$ | $CH_4$ | $C_2H_6$ | $C_3H_8$ | True value | Calorific value converted value | Error |
| A | 20.00 | 20.00 | 60.00 | | | 130.0 | 127.5 | −2.5 |
| B | 10.00 | 10.00 | 80.00 | | | 112.8 | 113.5 | +0.7 |
| C | 5.00 | 5.00 | 90.00 | | | 106.5 | 106.6 | +0.1 |
| D | 2.50 | 2.50 | 95.00 | | | 103.2 | 103.2 | 0.0 |
| E | 1.25 | 1.25 | 97.50 | | | 101.6 | 101.5 | −0.1 |
| F | 10.00 | 5.00 | 85.00 | | | 107.8 | 108.3 | +0.5 |
| G | 5.00 | 2.50 | 92.50 | | | 103.8 | 104.0 | +0.2 |
| H | 2.50 | 1.25 | 96.25 | | | 101.9 | 101.9 | 0.0 |
| I | 5.00 | 10.00 | 85.00 | | | 111.2 | 111.8 | +0.6 |
| J | 2.50 | 5.00 | 92.50 | | | 105.8 | 105.8 | 0.0 |
| K | 1.25 | 2.50 | 96.25 | | | 102.8 | 102.8 | 0.0 |
| L | 10.00 | 10.00 | 64.00 | 16.00 | | 81.9 | 79.6 | −2.3 |
| M | 5.00 | 5.00 | 72.00 | 18.00 | | 75.6 | 72.9 | −2.7 |
| N | 2.50 | 2.50 | 76.00 | 19.00 | | 72.3 | 69.6 | −2.7 |
| O | 1.25 | 1.25 | 78.00 | 19.50 | | 70.7 | 67.9 | −2.8 |
| P | 10.00 | 10.00 | 60.00 | 12.00 | 8.00 | 72.1 | 69.3 | −2.8 |
| Q | 5.00 | 5.00 | 80.00 | 6.00 | 4.00 | 78.7 | 77.1 | −1.6 |
| R | 2.50 | 2.50 | 90.00 | 3.00 | 2.00 | 84.7 | 83.8 | −0.9 |
| S | 1.25 | 1.25 | 95.00 | 1.50 | 1.00 | 89.7 | 89.9 | +0.2 |

From the results described above, according to the methane number calculation method of the present invention, for a sample gas composed mainly of a paraffinic hydrocarbon gas and containing a nitrogen gas and a carbon dioxide gas as miscellaneous gas components, it was confirmed that irrespective of the composition of the sample gas, a methane number value (an approximate solution) within a certain error range (within ±2.8) for the methane number according to the AVL Standard can be obtained.

Here, the measured methane numbers have no practical problem if the methane numbers fall within, for example, about ±3.0 of the methane number according to the AVL Standard.

INDUSTRIAL APPLICABILITY

The present invention is capable of detecting in real time variations in fuel property such as variations in methane number or variations in calorific value caused by variations in the gas composition of a natural gas serving as a fuel gas. Thus, the invention is expected to be very useful for combustion control of a natural gas fuel engine.

REFERENCE SIGNS LIST 10 outer container
11 inlet port for sample gas
12 inlet port for reference gas
13 gas outlet
20 calorific value measurement mechanism
21 refractive index converted calorific value measurement mechanism
22 refractive index measurement means
23 refractive index-to-calorific value conversion means
25 sonic speed converted calorific value measurement mechanism
26 sonic speed measurement means
27 sonic speed-to-calorific value conversion means
30 nitrogen concentration calculation mechanism
35 calorific value calculation mechanism
40 methane number calculation mechanism
45 display mechanism
50 carbon dioxide concentration measurement mechanism
51 carbon dioxide concentration measurement means

The invention claimed is:

1. A methane number calculation method comprising:
determining, for each of a plurality of reference gases, a particular relational expression between a methane number and a basic calorific value of the respective reference gas, each respective reference gas comprising a natural gas, the plurality of reference gases having different methane numbers;
continuously measuring a basic calorific value of a sample gas based on a refractive index converted calorific value obtained based on a refractive index of the sample gas and a sonic speed converted calorific value obtained based on a sonic speed of the sample gas;
measuring a concentration of nitrogen gas contained in the sample gas and a concentration of carbon dioxide gas contained in the sample gas, and
continuously calculating a methane number of the sample gas based on the particular relational expression, the basic calorific value of the sample gas, a first correction value associated with the concentration of the nitrogen gas, and a second correction value associated with the concentration of the carbon dioxide gas.

2. The methane number calculation method according to claim 1, wherein the particular relational expression is set forth below:

$$MN = f_{(Q')} + A$$

wherein:
MN is the methane number,
$f_{(Q')}$ is a selected one of formulas (a) through set forth below,
Q' represents the basic calorific value of the sample gas in MJ/m³,
A is a value between −2.0 and 2.0,
$X_{N2}$ is the concentration of nitrogen gas contained in the sample gas expressed in volume percentage [vol %], and
$X_{CO2}$ is the concentration of carbon dioxide as contained in the sample gas expressed in volume percentage [vol %], wherein $f_{(Q')}$ is selected based on the value of the basic calorific value;

$$f_{(Q')} = -0.529862Q'^3 + 67.1872Q'^2 - 2845.15Q' + 40316.8 + 0.32X_{N2} + 1.00X_{CO2} \quad (Q' \leq 42.0)$$ Formula (a)

$$f_{(Q')} = -0.006745Q'^3 + 1.11764Q'^2 - 62.9206Q' + 1252.43 + 0.32X_{N2} + 1.00X_{CO2} \quad (42.0 < Q' \leq 55.0)$$ Formula (b)

$$f_{(Q')} = -0.001547Q'^3 + 0.293255Q'^2 - 19.1911Q' + 475.981 + 0.32X_{N2} + 1.00X_{CO2} \quad (55.0 < Q' \leq 63.0)$$ Formula (c)

$$f_{(Q')} = -0.000278Q'^3 + 0.072315Q'^2 - 6.44881Q' + 232.610 + 0.32X_{N2} + 1.00X_{CO2} \quad (63.0 < Q')$$ Formula (d).

3. The methane number calculation method according to claim 1, wherein the basic calorific value of the sample gas is determined based on a refractive index converted calorific value obtained based on a refractive index of the sample gas and a sonic speed converted calorific value obtained based on a sonic speed of the sample gas.

4. The methane number calculation method according to claim 1, wherein the concentration of the carbon dioxide gas contained in the sample gas is measured by an infrared absorption method.

5. A methane number measurement device comprising:
a calorific value measurement component adapted to:
determine, for each of a plurality of reference gases, a particular relational expression between a methane number and a basic calorific value of the respective reference gas, each respective reference gas comprising a natural gas, the plurality of reference gases having different methane numbers;
continuously measure a basic calorific value of a sample gas;
measure a concentration of a carbon dioxide gas contained in the sample gas; and
calculate a concentration of a nitrogen gas contained in the sample gas;
a first inlet adapted to supply the sample gas to the calorific value measurement component;
a second inlet port adapted to supply the reference gas to the calorific value measurement component; and
a methane number calculation component adapted to:
continuously calculate a methane number of the sample gas based on the particular relational expression, the basic calorific value of the sample gas, a first correction value associated with the concentration of carbon dioxide gas, and a second correction value associated with the concentration of nitrogen gas.

6. The methane number measurement device according to claim 5, wherein the particular relational expression is described below:

$$MN = f_{(Q')} + A$$

wherein:
MN is the methane number,
$f_{(Q')}$ is formulas (a) through (d) set forth below,
Q' represents the basic calorific value of the sample gas in MJ/m³,
A is a value between −2.0 and 2.0,
$X_{N2}$ is the concentration of nitrogen gas contained in the sample gas expressed in volume percentage [vol %], and
$X_{CO2}$ is the concentration of carbon dioxide gas contained in the sample gas expressed in volume percentage [vol %],
wherein $f_{(Q')}$ is selected based on the value of the basic calorific value;

$$f_{(Q')} = -0.529862Q'^3 + 67.1872Q'^2 - 2845.15Q' + 40316.8 + 0.32X_{N_2} + 1.00X_{CO_2}(Q' \leq 42.0) \quad \text{Formula (a)}$$

$$f_{(Q')} = -0.006745Q'^3 + 1.11764Q'^2 - 62.9206Q' + 1252.43 + 0.32X_{N_2} + 1.00X_{CO_2}(42.0 < Q' \leq 55.0) \quad \text{Formula (b)}$$

$$f_{(Q')} = -0.001547Q'^3 + 0.293255Q'^2 - 19.1911Q' + 475.981 + 0.32X_{N_2} + 1.00X_{CO_2}(55.0 < Q' \leq 63.0) \quad \text{Formula (c)}$$

$$f_{(Q')} = 0.000278Q'^3 + 0.072315Q'^2 - 6.44881Q' + 232.610 + 0.32X_{N_2} + 1.00X_{CO_2}(63.0 < Q') \quad \text{Formula (d)}.$$

7. The methane number measurement device according to claim 5, further comprising:
   a refractive index converted calorific value measurement unit configured to determine a refractive index converted calorific value from a refractive index value of the sample gas;
   a sonic speed converted calorific value measurement unit configured to determine a sonic speed converted calorific value from a sonic speed value of the sample gas; and
   a calorific value calculation unit configured to calculate the basic calorific value of the sample gas based on a basis of the refractive index converted calorific value, the sonic speed converted calorific value, the concentration of the carbon dioxide gas, and the concentration of the nitrogen gas.

8. The methane number measurement device according to claim 5, further comprising an infrared sensor.

\* \* \* \* \*